(12) United States Patent
Eros et al.

(10) Patent No.: US 9,757,360 B2
(45) Date of Patent: Sep. 12, 2017

(54) PHARMACEUTICAL COMPOSITION COMPRISING A RYANODINE RECEPTOR ANTAGONIST FOR FACILITATING WOUND HEALING

(71) Applicant: SZEGEDI TUDOMÁNYEGYETEM, Szeged (HU)

(72) Inventors: Gábor Eros, Szeged (HU); Döníz Degovics, Szeged (HU); Petra Hartmann, Szeged (HU); Lajos Kemény, Szeged (HU)

(73) Assignee: SZEGEDI TUDOMÁNYEGYETEM, Szeged (HU)

( * ) Notice: Subject to any disclaimer, the term of this patent is extended or adjusted under 35 U.S.C. 154(b) by 0 days.

(21) Appl. No.: 15/103,374

(22) PCT Filed: Dec. 12, 2014

(86) PCT No.: PCT/HU2014/000124
§ 371 (c)(1),
(2) Date: Jun. 10, 2016

(87) PCT Pub. No.: WO2015/087097
PCT Pub. Date: Jun. 18, 2015

(65) Prior Publication Data
US 2016/0303085 A1 Oct. 20, 2016

(30) Foreign Application Priority Data

Dec. 12, 2013 (HU) ..................................... 1300720

(51) Int. Cl.
*A61K 45/06* (2006.01)
*A61K 31/4178* (2006.01)
*A61K 9/00* (2006.01)

(52) U.S. Cl.
CPC ........ *A61K 31/4178* (2013.01); *A61K 9/0014* (2013.01); *A61K 45/06* (2013.01)

(58) Field of Classification Search
None
See application file for complete search history.

(56) References Cited

U.S. PATENT DOCUMENTS 4,049,650 A * 9/1977 White, Jr. ............ C07D 233/88
548/236
5,132,119 A * 7/1992 Lee ........................ A61K 31/00
424/646

(Continued)

FOREIGN PATENT DOCUMENTS

JP 2007-308403 A 11/2007
JP 2011-250728 A 12/2011

OTHER PUBLICATIONS

Zucchi et al., Pharmacological reviews. 49 (1): 1-51 1997.*

(Continued)

*Primary Examiner* — Karl J Puttlitz
(74) *Attorney, Agent, or Firm* — Jason D. Voight (57) ABSTRACT

The invention relates to the use of pharmaceutical compositions containing as the active agent a compound of formula I in the treatment of dermal wounds. The compositions may be used for the promotion of healing of wounds affecting the deeper layers under the epithelium, including dermal- and sub dermal connective tissue, being cut, punctured, sliced wounds or originating in insufficient tissue perfusion, chronic diseases or other harms. The compositions are formulated for local application and may comprise other active agents contributing to wound healing in addition to a compound of formula (I).

(Continued)

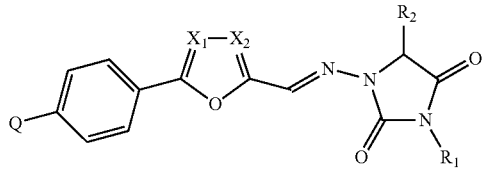

(I)

9 Claims, 4 Drawing Sheets (56) References Cited

U.S. PATENT DOCUMENTS

2009/0306163 A1 12/2009 Lipkin
2013/0261058 A1 10/2013 Schally et al.

OTHER PUBLICATIONS

Database Caplus Chemical Abstracts Service, Columbus, Ohio, US; Database Accession No. 2004:93663, Abstract of Bhaskar et al., Indian Journal of Physiology and Pharmacology (2004), 48(1), 111-114.*

Database Caplus Chemical Abstracts Service, Columbus, Ohio, US; Database Accession No. 2010:214391, Abstract of Patil et al., Pharmacologyonline (2009), (2), 1125-1135.*

Denda et al.: "Ryanodine Receptors Are Expressed in Epidermal Keratinocytes and Associated with Keratinocyte Differentiation and Epidermal Permeability Barrier Homeostasis", Journal of Investigative Dermatology, 2011, vol. 132, pp. 69-75.

Parness: "The Dantrolene Binding Site on RYR1 Implications for clinical therapy", Springer Science, 2005, pp. 243-251.

* cited by examiner

PHARMACEUTICAL COMPOSITION COMPRISING A RYANODINE RECEPTOR ANTAGONIST FOR FACILITATING WOUND HEALING

This is the national stage of International Application PCT/HU2014/000124, filed Dec. 12, 2014.

FIELD OF THE INVENTION

The invention relates to pharmaceutical compositions comprising a compound of formula (I) for use in the treatment of dermal wounds. The topical pharmaceutical composition may be used for the treatment of wounds affecting the deeper layers of the skin, including connective tissue. The pharmaceutical composition may comprise other active agents contributing to wound healing in addition to the compound of formula I.

STATE OF THE ART

The skin is the largest organ in humans providing protection against physical and chemical harm and causative agents. Hence, the appropriate healing of dermal wounds is necessary for the homeostasis. Wound regeneration is a complex process which requires a well-orchestrated interaction of different cell types.

Several topical formulations are known for the treatment of dermal wounds. Most of them promote the healing of superficial wounds and abrasions by facilitating epithelialization and exerting antibiotic- and anti-inflammatory effects (e.g. dexpanthenol containing formulations which facilitate epithelialization in burns and irritation and may be used as a supplemental therapy for chronic wounds, too).

Antimicrobial tinctures (e.g. povidone iodide, ethylhexyl-glycerol) and disinfectant solutions (e.g. hydrogen peroxide) eliminate causative agents but may also damage the epidermis and the dermis. Further, residual disinfectants in the wound may lead to irritation, inflammation.

Hyaluronate containing formulations promote tissue renewal and can be used for the acceleration of normal wound healing such as for the therapy of chronic wounds. Antibacterial agents (e.g. zinc, silver-sulfadiazine) are often added to hyaluronate containing formulations.

Joint application of fibrinolizine and dezoxiribonuclease leads to the decay of damaged cells resulting in clean wound surfaces which contributes to a better healing. The field of application comprises infected wounds or wounds carrying the risk of infection, chronic wounds and ulcers. Formulations containing collagenases or proteases have the same mechanism of action. If the wound is treated with disinfectant prior to their application, enzymes may be inactivated by the disinfectant as a result of inappropriate rinsing. Moreover, enzymes may irritate the healthy tissue surrounding the wound.

Sodium samarium disulfosalicilate, a non-steroid anti-inflammatory drug (NSAID) is applied in certain forms of acute dermatitis.

In clinical practice, negative pressure wound therapy, NO, hyperbaric oxygen, $CO_2$ and growth factors can also be applied in the treatment of chronic wounds. (Daróczy et al., 2011).

Dantrolene is a derivative of hydantoin, known since the 1960ies. This compound inhibits muscle contractility particularly in striated muscles through its effect on ryanodine receptors. However, the mentioned effect is characteristic of the heart and smooth muscle, as well. The original indication of dantrolene is muscle relaxation. In the USA and many European countries it is on market as a muscle relaxant especially for spastic conditions in which other drugs fail to work.

It has been described in the seventies that dantrolene is effective in the treatment of malignant hyperthermia which is a life-threatening complication of anesthesia originating in a mutation of ryanodine receptor type I. Until now, dantrolene is the only effective therapy for this disorder (Harrison, 1975). Malignant hyperthermia is the major indication for the use of dantrolene, but it may be applied in the treatment of neuroleptic malignant syndrome and ecstasy intoxication, too.

The Hungarian National Institute of Pharmacy recommends dantrolene for the treatment of malignant hyperthermia only (see the description on the website of the Institute).

US 20090306163 patent application reveals a dantrolene-containing cosmetic product which may be suitable for the prevention or treatment of wrinkling by muscle relaxant effect of dantrolene.

JP2007308403 patent application describes a dantrolene-containing medical product which can be applied locally in inflammatory disorders and burns. This invention utilizes the muscle relaxant effect of dantrolene, because muscle relaxant drugs soothe muscle contraction following the damage, improve microcirculation and reduce inflammation.

JP2011250728 patent application describes a method for the screening of compounds which may regenerate impaired barrier function after superficial injuries or due to skin aging. Agents identified by the method may be used in cosmetic products which prevent dehydration of the skin. The advantage of the method is that it may replace animal experiments in testing ingredients of cosmetic products. The method has identified compounds which inhibit the ryanodine receptors. Thus, the examples mention dantrolene which is an antagonist of ryanodine receptors.

According to the data obtained in animal experiments by Denda and coworkers (Denda et al., 2012), local application of dantrolene accelerates barrier regeneration after removal of the uppermost layer of the epidermis.

In the course of our research activity, it has unexpectedly been recognized that dantrolene positively affects the healing of large, full-thickness dermal wounds.

DEFINITIONS

Dermal wound, as used herein is a discontinuity of the skin, and optionally, that of the skin and the underlying tissues. Wounds may be simple or complex. Simple, superficial- or moderately deep wounds affect the skin, while complex or deep wounds may affect the underlying muscles, nerves, bones and vessels as well. The term dermal wound is used herein for both acute and chronic, difficult-to-heal wounds. Full-thickness wounds are wounds affecting each layer of the skin inclusive connective tissue, and optionally connective tissue under the skin.

Skin tissue (briefly skin) is an extended organ with barrier function comprising the following 3 layers: epidermis, dermis and subcutis.

Epidermis is a keratinized stratified squamous epithelium, the cells of which are continuously being replaced from the stratum basale. Melanocytes can also be found in the epidermis. In the present description, the upper layer of the skin refers to the epidermis or its uppermost cellular layers.

Dermis consists of loose connective tissue and contains vessels, nerve endings and skin appendages (hair follicles, sebaceous glands and sweat glands).

Hypodermis contains connective tissue and fat.

Subject is a human or another vertebrate in need of a treatment promoting the healing of the dermal wound.

(Wound) Dressing is defined as an interactive product which can be utilized in wound treatment. Interactive dressings build a physical or chemical interaction with the wound. This category comprises hydrogels, hydrocolloids, alginate-based bandages, film and matrix bandages and impregnated meshes.

Throughout the description, the terms comprise(s), comprising indicate that an object comprising something may comprise other components, as well. Thus, a list of one or more elements following the verb "comprise(s)", "comprising" does not exclude the presence of other components. E.g. a medical product which comprises an active substance may also comprise other agents or any type of additives. A special variation of the verb consist is essentially consisting of something which means that an object comprising the listed components, comprises beyond the list only such components which do not contribute to its main effect. For example, a medical product, which essentially consists of a certain active agent, may contain additives that do not change (especially not substantially) the biological effect, but the product does not comprise any other active agent.

In the description, the use of singular forms or definite articles does not exclude the interpretation as plural on determination of the scope of protection, unless it is indicated or the context suggests contrariwise.

The terms "one", "a", or "an", unless otherwise indicated or where the context requires otherwise are used as an indefinite article and not as a numeral.

BRIEF DESCRIPTION OF THE INVENTION

The invention relates to a pharmaceutical composition for use in the treatment of a dermal wound in a subject in need of such a treatment, wherein the pharmaceutical composition comprises as an active agent a ryanodine receptor antagonist compound of general formula (I), (I)

wherein in formula (I)

Q is an electron withdrawing group preferably selected from halogen atoms, preferably Br, Cl or F; pseudohalogen, such as azido, thiocyano, or cyano; nitro, unsubstituted amino, substituted amino, preferably methylamino, ethylmethylamino or dimethylamino; hydroxy, $C_{1-4}$ alkyloxy, preferably methyloxy or ethyloxy;

$X_1$ and $X_2$ are (a) sp2 carbon atoms to which a H or methyl is attached or (b) sp2 nitrogen atom, wherein preferably when $X_1$ is defined by (b), $X_2$ is defined by (a) and when $X_2$ is defined by (b), $X_1$ is defined by (a) or both $X_1$ and $X_2$ are defined by (a)

$R_1$ is a hydrogen atom, $C_{1-4}$ alkyl, $C_{2-4}$ alkenyl, the alkyl or alkenyl being unsubstituted or substituted, wherein the substituent is preferably selected from the group consisting of halogen atoms, preferably I, Br, Cl or F; azido, amino, which may be unsubstituted or substituted, preferably methylamino, ethylmethylamino or dimethylamino; or $R_1$ is aryl or heteroaryl, preferably phenyl, benzyl or tolyl, which is unsubstituted or substituted with a substituent preferably selected from the group consisting of halogen atoms, preferably I, Br, Cl or F; azido, amino, which may be unsubstituted or substituted, preferably methylamino, ethylmethylamino, or dimethylamino, and $R_2$ is a hydrogen atom, hydroxy, $C_{1-4}$ alkyloxy, preferably methyloxy or ethyloxy; unsubstituted or substituted $C_{1-4}$ alkyl, wherein the substituent is preferably selected from the group consisting of halogen atoms, preferably I, Br, Cl or F; azido, amino, which may be unsubstituted or substituted, preferably methylamino, ethylmethylamino or dimethylamino;

or a pharmaceutically acceptable salt thereof, such as a sodium salt thereof and a pharmaceutically acceptable vehicle, carrier and/or excipient.

In a preferred embodiment the active agent of the composition is a compound of general formula (I), wherein in formula (I)

Q is an electron withdrawing group preferably selected from halogen atoms, preferably Br, Cl or F; pseudohalogen, such as azido, thiocyano, or cyano; nitro, unsubstituted amino, substituted amino, preferably methylamino, ethylmethylamino or dimethylamino; hydroxy, $C_{1-4}$ alkyloxy, preferably methyloxy or ethyloxy;

$X_1$ and $X_2$ are (a) sp2 carbon atom to which a H or methyl is attached or (b) sp2 nitrogen atom, wherein preferably when $X_1$ is defined by (b), $X_2$ is defined by (a) and when $X_2$ is defined by (b), $X_1$ is defined by (a) or both $X_1$ and $X_2$ are defined by (a), $R_1$ is a hydrogen atom, $C_{1-4}$ alkyl, $C_{2-4}$ alkenyl, the alkyl or alkenyl being unsubstituted or substituted, wherein the substituent is preferably selected from the group consisting of halogen atoms, preferably I, Br, Cl or F; azido, amino, which may be unsubstituted or substituted, preferably methylamino, ethylmethylamino or dimethylamino; or $R_1$ is $C_{6-14}$ aryl or $C_{4-14}$ heteroaryl, wherein the heteroaryl comprises 1 to 5, preferably 1 to 3 heteroatoms selected from N, O, S; wherein the aryl or heteroaryl may be unsubstituted or substituted with a substituent preferably selected from the group consisting of methyl, ethyl, propyl, isopropyl, halogen, preferably I, Br, Cl or F; azido, hydroxy, amino, which is unsubstituted or substituted, preferably methylamino, ethylmethylamino or dimethylamino, and/or optionally $R_1$ is not H, $R_2$ is a hydrogen atom, hydroxy, $C_{1-4}$ alkyloxy, preferably methyloxy or ethyloxy; unsubstituted or substituted $C_{1-4}$ alkyl, wherein the substituent is preferably selected from the group consisting of halogen atoms, preferably I, Br, Cl or F; azido, hydroxy, amino, which is unsubstituted or substituted, preferably methylamino, ethylmethylamino or dimethylamino;

or a pharmaceutically acceptable salt thereof.

Preferably, when Q is a substituted amino, Q is attached via the N of the amino group and/or when Q is alkoxy, Q is attached via the 0 of the alkoxy group.

In a preferred embodiment in the formula of the compound according to general formula (I)

Q is selected from Br, Cl or F, azido, nitro and amino, both $X_1$ and $X_2$ are =CH— (sp2 carbon atom to which a H atom is attached), $R_1$ is H, methyl or ethyl, $R_2$ is H or hydroxy, or a pharmaceutically acceptable salt thereof.

Preferably, in the formula of the compound according to general formula (I)

Q is selected from Br or Cl, nitro and amino, both $X_1$ and $X_2$ are =CH— (sp2 carbon atom to which a H atom is attached), $R_1$ is H or methyl, $R_2$ is H or hydroxy, or a pharmaceutically acceptable salt thereof.

The active agent in the pharmaceutical composition according to the invention is highly preferably selected from the group consisting of azumolene, hydroxy dantrolene, amino dantrolene and dantrolene and a pharmaceutically acceptable salt thereof. The compound is preferably or highly preferably dantrolene or a pharmaceutically acceptable salt thereof.

The compound of the invention is a ryanodine receptor (RyR) antagonist. Preferably, the compound of the invention increases blood flow, particularly the blood flow of the wound edges and in capillaries, particularly as monitored by Laser Doppler. The compound of the invention preferably increases the diameter of blood vessels, particularly as monitored by IVM (intravital video microscopy).

Preferably, the dermal wound is a wound that extends into a layer under the epidermis.

Highly preferably, the dermal wound extends into all layers of the skin, including connective tissue, optionally connective tissue under the skin.

Highly preferably, the dermal wound is associated with a chronic disease, wherein the chronic disease is preferably diabetes mellitus.

The dermal wound is preferably not a burn. Preferably, the dermal wound is not a wound that may or should be treated by a method identical to a treatment method for a burn wound, particularly not a frostbite, a wound caused by electric shock, or a wound caused by a corrosive chemical. Highly preferably, the wound is not a wound to be treated basically or principally by a treatment method against inflammation or a wound that is to be treated basically or principally with a muscle relaxant agent.

According to a preferred embodiment the pharmaceutical composition is formulated for topical use. The pharmaceutical composition may be in the form of an ointment, creme, gel, spray, talcum, foam composition, patch, wound dressing, solution or suspension.

The pharmaceutical composition may further comprise another agent useful in the healing of wounds. The additional agent useful in wound healing is e.g. selected from analgesic compounds, circulation enhancer compounds, anti-inflammatory compounds, compounds with a muscle relaxant effect, antibacterial compounds, antimicrobial compounds, enhancers of tissue forming, compounds that facilitate the degradation of damaged or dead cells, growth factors, disinfectants.

The subject is preferably a vertebrate animal, highly preferably a mammal, particularly preferably a human.

According to a further embodiment the invention relates to a method for the treatment of dermal injuries in a subject in need of such a treatment, wherein the damaged area of the skin is contacted with a compound of general formula (I)

wherein Q, $X_1$, $X_2$, $R_1$ and $R_2$ of the formula are defined herein, e.g. above.

Preferably, the dermal wound of the method of the invention is a wound that extends into a layer under the epidermis.

Highly preferably, the injury of the skin extends to all layers of the skin, including connective tissue, optionally connective tissue under the skin.

Highly preferably, the dermal wound is associated with a chronic disease, wherein the chronic disease is preferably diabetes mellitus.

According to a preferred embodiment the compound of formula (I) is delivered to the injured skin in the form of a pharmaceutical composition. Highly preferably the composition is formulated for topical use. The pharmaceutical composition may be in the form of an ointment, cream, gel, spray, talcum, foam composition, patch, wound dressing, solution or suspension.

Highly preferably, the composition is delivered to the injured skin surface 1 to 10 times daily, preferably 1 to 4, highly preferably 2 to 3 times daily.

Highly preferably, the pharmaceutical composition described herein is used in the method of the invention.

SHORT DESCRIPTION OF THE FIGURES

Each Figure depicts median values with $25^{th}$ and $75^{th}$ percentiles. In each Figure, X means p<0.05 vs control, Da: dantrolene-treated group, control: saline-treated control group.

DETAILED DESCRIPTION OF THE INVENTION

The human skin consists of three layers: epidermis, dermis and subcutis. The epidermis is a multi-layer stratified squamous epithelium in which cells are continuously replenished from the stratum basale. Melanocytes are also found in the epidermis. The base of the dermis is a loose connective tissue containing vessels, nerve endings and skin appendages (e.g. hair follicles, sebaceous glands and sweat glands). Fatty tissue can be found among the tissue fibres of the subcutis. Herein, we define the top layer of the skin as the epidermis or the upper cell layers of the epidermis.

Dermal wounds, extending into the upper layers of the skin, preferably the layers under the epidermis, are frequent and according to the state of the art there is a need for further therapeutic approaches.

Dermal wounds, treated according to the method of the invention, may be superficial wounds affecting the epidermis and the directly underlying layer or moderately deep wounds penetrating to the dermis. Complex or deep dermal wounds affect not only the skin but may also extend to the muscle layer, nerves, bones and vessels under the skin. Concerning etiology, dermal wounds may originate in abrasion, slice, cutting, puncturing, crushing, laceration, biting, inadequate blood supply (e.g. atherosclerosis related ulcus), chronic diseases (e.g. foot ulcer due to diabetes), necrosis (e.g. decubitus), thermic harms (e.g. burns), and chemical challenges (e.g. acids) or other impacts. According to certain preferred embodiments, the dermal wound is not a thermic (e.g. burn) wound or a wound of the same mechanism or a wound requiring the same treatment as a burn wound. The term dermal wound as used herein may refer to both acute and chronic (difficult-to-heal) wounds. Preferably, the wound is a full thickness dermal wound. Full thickness wounds affect each layer of the skin, including connective tissue of the dermis and, optionally, that of the subcutis.

To our best knowledge, the background art does not offer any information regarding the effects of dantrolene or those of other compounds acting as antagonist of ryanodine receptors, described in the present invention, in the skin layers under the uppermost layer of the epidermis, and preferably in layers under the epidermis and tissue layers under the skin. It has not yet been clarified what kind of ryanodine receptors occur in the deeper layers of the skin, and therefore, no information is available on their distribution and physiological role in these tissues.

One skilled in the art can test the activity of an agent as a ryanodine receptor antagonist without undue difficulties. Appropriate methods are described by Jaggar et al., 1998, Arendshorst & Thai, 2009, Denda et al., 2012 and other publications cited by the the authors. It is known that ryanodine receptors play different roles in different organs and tissues. Although ryanodine receptors were found first in muscle tissue, it has been recognized that they appear in other tissues, as well. Their most extensively studied role is the connection of excitation and contraction, but they can be found in non-excitatory cells, too. Ryanodine receptor type 1 (RyR-1) is characteristic of striated muscle, type 2 (RyR-2) can be found in cardiac muscle but has been described in Langerhans islets, too. Ryanodine receptors type 1 and 3 were proven to be present in leukocytes. Ryanodine receptor type 3 (RyR-3) was first identified in the mammalian brain, but according to the present knowledge its occurrence may be considered universal, it can be found in the skin, striated muscle, smooth muscle and leukocytes although at lower quantities and its role is not fully clarified. RyR-1 and RyR-2 are also expressed in the brain. However, the pattern of their expression is different. RyR-1 appears abundantly in Purkinje cells of the cerebellum, RyR-2 is expressed predominantly in the dentate gyrus while RyR-3 in the pyramid cells of hippocampus (Ca1 region), the basal ganglia and the olfactory bulb. All isoforms are present in smooth muscle cells (Kushnir et al., 2010).

Ryanodine affects the mechanism of contraction differently in striated muscle and cardiac muscle. In striated muscle, it induces contractions leading to tetanic spasms, while it may result in cardiac arrest via decreasing the contractility in the heart. Although both effects are based on calcium release, the activity of calcium-scavenging mechanisms are different in striated muscle and cardiac muscle.

It has been described that ryanodine receptors can be found in vessels of different caliber in several organs, e.g. in the kidney (Arendshorst & Thai, 2009), urether, spermatic duct, mesenteric artery (Borisova et al., 2009), striated muscle (cremaster muscle) (Westcott & Jackson, 2011) and the brain (Dabertrand et al., 2012). Ryanodine receptors influence the intracellular calcium level in the vascular smooth muscle hereby regulating vascular tonus. However, they may play a different role in different organs. Inhibition of ryanodine receptors was found to lead to vasoconstriction (Jaggar et al., 1998). However, inhibition of ryanodine receptors may soothe the existing vasoconstriction in the kidney (Arendshorst & Thai, 2009). Caffeine, which activates the ryanodine receptors, leads to vasoconstriction in cerebral and meningeal vessels (Dabertrand et al., 2012, Knot et al., 1998). Nutritive arteries of the muscle tissue display vasodilatation due to inhibition of ryanodine receptors (Westcott & Jackson, 2011).

A paper published by Denda et al. (Denda et al., 2012) and patent application JP 2011250728 reveal that dantrolene and 1,1-diheptyl-4,4bipyridinium-dibromide (DHBP), another known antagonist of ryanodine receptors, ameliorate transepidermal water loss in mice in which barrier function is impaired after tape stripping of the upper epidermis. The authors have shown by means of immunohistochemistry that ryanodine receptors are present on the keratinocytes. Furthermore, expression of all isotypes (at mRNA level) is more pronounced in differentiated keratinocytes. RyR-1 and RyR-2 are localized in the upper layer of the epidermis. Accordingly, the authors presumed that the promotion of barrier reconstruction induced by dantrolene and DHBP originates in the inhibition of ryanodine receptors.

As far as we know, no data are available concerning the role of ryanodine receptors on dermal circulation and their impact on dermal injuries affecting layers under the upper part of epidermis.

In our experiments, we have studied the effects of dantrolene on different parameters of wound healing. SKH-1 hairless male mice were used in the experiments. Full-thickness wound was made in a dorsal skin fold. The effects of dantrolene or saline (control group) on wound healing were monitored by means of photo documentation, intravital videomicroscopy (IVM) and laser Doppler flowmetry. The experimental setup was in accordance with the model described by Sorg et al. (Sorg et al., 2007). Wounds were treated daily either with dantrolene or with saline.

Unexpectedly, our findings have shown that dantrolene accelerated the wound closure and decreased the number of leukocyte-endothelial interactions. Another unexpected effect was that dantrolene increased blood flow in the wound edges, evaluation of IVM records revealed significantly higher vessel diameters in dantrolene-treated animals than in control ones. Higher red blood cell velocities were measured in the capillaries. Laser Doppler flowmetry unraveled considerably higher blood flow as compared to baseline values. This microcirculation-improving effect of dantrolene was detected in two different tissue layers which, in view of the above mentioned published data, was not predictable.

IVM visualized the dermal vessels of the wound edges and showed that application of dantrolene increases vessel diameters, while laser Doppler sensor was placed onto the basis of the wound and blood flow in the muscle layer of the skin fold's opposite side was monitored. This examination showed elevated blood flow in the muscle.

Macroscopic wound closure was assessed by evaluation of photographs with a special software. Histology was used for characterization of epithelialization and dermal regeneration. Macroscopic wound closure reached nearly 100% in both groups. Rate of wound closure in the dantrolene-treated group was significantly higher on days 4, 8 and 12 than in the control group. Faster dermal regeneration induced by dantrolene is an unexpected result, because no information was available previously on regenerative or any other effects of dantrolene and/or ryanodine receptors in the lower layers of the skin. Ryanodine receptors mediate diverse effects in different tissues and the same ligands may induce distinct effects on different isoforms. Thus, effects of dantrolene on wounds penetrating into the deeper layers of the skin were not predictable for one skilled in the art prior to the experiments.

Based on our experiments, dantrolene exerts its beneficial effects through the vasculature and microcirculation of the dermis and the muscle layer. Although based on the findings described in patent application JP 2011250728 and of Denda and co-workers (Denda et al., 2012), the effect of dantrolene to the barrier function and regeneration of the epidermis could have been speculated, no patent (application) or manuscript describes the effect of dantrolene—or any other ryanodin-antagonist—on the circulation of neighboring vessels of wounds. Hence, this effect of dantrolene and its role in wound healing are novel and unforeseen results of our experiments.

The composition useful for wound healing referred to in patent application JP 2011250728 contains dantrolene, but based on its description the skilled artisan would have not deducted the conclusion which is described herein. The composition described in patent application JP 2011250728 is a muscle relaxant, which is used against inflammation, but not directly for the purpose of wound healing, although it was applied on skin wounds, the healing of which was depending on inflammatory processes, too.

Dantrolene—like other muscle relaxants described in patent application JP 2011250728—reduces inflammation through its muscle-relaxant effect by inhibiting the post-injury muscle control. However, in the present invention healing of skin wounds where the muscle control has no significance, is facilitated, since in the experimental model we used not only the upper and middle layer of skin tissue but the muscle layer below were removed as well. Therefore, according to the present invention, the effect of dantrolene on wound healing cannot be explained by its muscle relaxant effect.

In our experiments, excised wound was formed, the healing tendency of which differs from combustion wounds disclosed in JP 2007308403. Reducing inflammation, such as by the use of steroids, is recommended in case of minor combustion wounds, while in wounds of other origin steroids worsen healing tendency. Accordingly, reducing inflammation does not obviously result in improved wound healing.

Based on our experimental results, we may rightly assume that dantrolene will exert the same effect on wound healing in case of wounds similar to those in the above described experiments, such as diabetes mellitus and cardiovascular failure-related slow healing and chronic wounds. In support of our hypothesis we have designed the following experiment: application of dantrolene to promote wound healing in a skin fold chamber model after inducing diabetes by streptozotocin in mice.

Diabetes is induced with intraperitoneal (i.p.) injections of streptozotocin (5×50 mg/kg) according to literature data (Lee et al., 2014, Langer et al., 2002). After 5 weeks, the blood glucose content is measured and animals with 16.6 and 33.2 mmol/L glucose level are enrolled to the experiment. Wounds of standard size are made on the dorsal part of the ear. Wound healing will be investigated according to the methods described in the examples and mentioned above.

The pharmaceutical composition according to the invention may be used as a topical formulation. The formulation may be e.g. an ointment, cream, gel, talcum, foam composition, patch, wound dressing (such as a hydrogel, film bandage, mesh combined with alginate, impregnated with a cream), solution or suspension. Administration may be as usual to the applied formulation or different; e.g. an ointment may be spread to the skin in a thin layer once or multiple times daily, a solution may be dripped into the wound once or multiple times a day to wet the wound, a patch or wound dressing may be changed to cover the wound multiple times a day or week.

The concentration of the active agent in the pharmaceutical composition according to the invention depends on the formulation and the indication for application. It might be e.g. 1 to 100 mg/kg for a cream, 1-100 mg/ml or 1 to 1000 µM or preferably 10 to 500 µM for a solution.

Treating dermal wounds and determining the method of treatment in the light of the active agent and its effect is implicit in the knowledge of one skilled in the art. Further information regarding the treatment of dermal wounds is to be found in Cathy Thomas Hess "Clinical Guide to Skin and Wound Care" 7. ed. 2012, and Avi Shai and Howard I. Maibach "Wound Healing and Ulcers of the Skin—Diagnosis and Therapy—The Practical Approach" 2005, and: "A nem gyógyuló (krónikus) börsebek ellátásának elöirányzott irányelve." A Börgyógyász Szakmai Kollégium jóváhagyásával készült irányelv 2011. átdolgozott formája. ("Guidelines to the therapy of non-healing (chronic) dermal wounds". Revised version of the Guidelines (2011) approved by the Hungarian College of Dermatology.

EXAMPLES

Example 1. The Effects of Dantrolene on the Healing of Full-Thickness Dermal Wounds in Mice The experiments were performed on male SKH-1 hairless mice of our own rearing (body weight: 36-44 g). Procedures and protocols were approved by the competent authorities (license number: V./145/2013.). Only healthy animals free of any type of injury were used, mice with any sign of disorders were discarded. Prior to the interventions the animals were anesthetized with a mixture of ketamine (Sigma) (90 mg/kg) and xylazine (Sigma) (25 mg/kg) administered intraperitoneally. A skin fold was formed in the dorsal region and was fixed with two symmetrical, fenestrated titanium plates (IROLA GmbH, Schonach, Germany) according to the description of Sorg et al. (Sorg et al., 2007).

Interventions and Treatments:

In the midline of the dorsal region two holding stitches were placed in order to form a skin fold. This skin fold was sandwiched by two symmetrical, fenestrated titanium plates. The plates were fixed with sutures, bolts and nuts. On one side of the skin fold, a circular full-thickness wound was made by removing the tissue down to muscle layer of the other side (the diameter of the wound was 4 mm while those of used for Laser-Doppler flowmetry came to 11 mm). The wound was covered with a glass coverslip incorporated into the window of the titanium frame. The glass was removed for the duration of treatments and measurements only. In the control group (n=6), the wounds were treated with 100 µL of sterile saline once a day while in the dantrolene-treated group (n=6) 100 µL of a solution containing the sodium salt of dantrolene (100 µM) was applied to the wound once a day (the salt was dissolved in sterile saline). The observation period took 20 days (according to our previous results this is the time period needed for approximately 100% closure of wounds of 4 mm).

Examinations:

Macroscopic wound closure. Photographs of the wounds were taken immediately after surgery and on days 4, 8, 12, 16 and 20. Circumstances of photographing were standardized (same light sources and distances). The images were evaluated with a software developed by our working group (DermAssess©). This software is an accessory function to the ImageJ software and enables the determination of color intensity (Eros et al., 2014) and the area measurement after calibration. Decrease in the wound area relative to the baseline value is given as percentage.

Intravital videomicroscopy (IVM). Microcirculation of the wound edges was monitored by means of IVM on days 4, 8 and 12. After anesthesia, 80 µL of a solution of fluorescein-isothyocyanate (FITC) labeled dextrane (2%) and also 80 µL of a solution of rhodamine-6G was administered retrobulbar. These contrast materials allow us to visualize microcirculation and leukocyte-endothelial interactions at the appropriate wavelengths. Video records of the microcirculation were evaluated off-line with Pictron IVM software. Red blood cell velocity (RBCV) was determined in the capillaries, the diameter of each vessel in the evaluated fields-of-view was measured (only diameters above 6 µm were considered) and sticking leukocytes were counted in the postcapillary venules (this parameter is relative to the area of the vessel wall and is given as cell/µm2).

Laser-Doppler flowmetry. In a further group (n=6), the animals were anesthetized on day 1 after wound creation. The sensor of the Laser-Doppler equipment was placed onto the wound. The sensor was removed after 10 minutes of measurement and 200 µL of dantrolene solution was applied to the wound. Another measurement was performed 10 minutes later.

Histology. On days 4 and 20 groups of control- and dantrolene-treated animals were sacrificed, the wounds were then excised, fixed in a solution of formaldehyde, embedded in paraffin and stained with hematoxylin and eosin. The Pannoramic Viewer software was used for the evaluation. Zone of epithelialization was defined as the extension of epithelial regeneration measured from the wound edges and given as percentage relative to the initial diameter of the wound. Dermal regeneration was determined, too (thickness of dermal connective tissue was measured within the wound area and was given as percentage relative to that of determined in the intact skin).

Statistical Analysis of the Results

Control- and dantrolene-treated groups were compared with the Mann-Whitney test and $p<0.05$ was considered statistically significant.

Results

Figure 1:
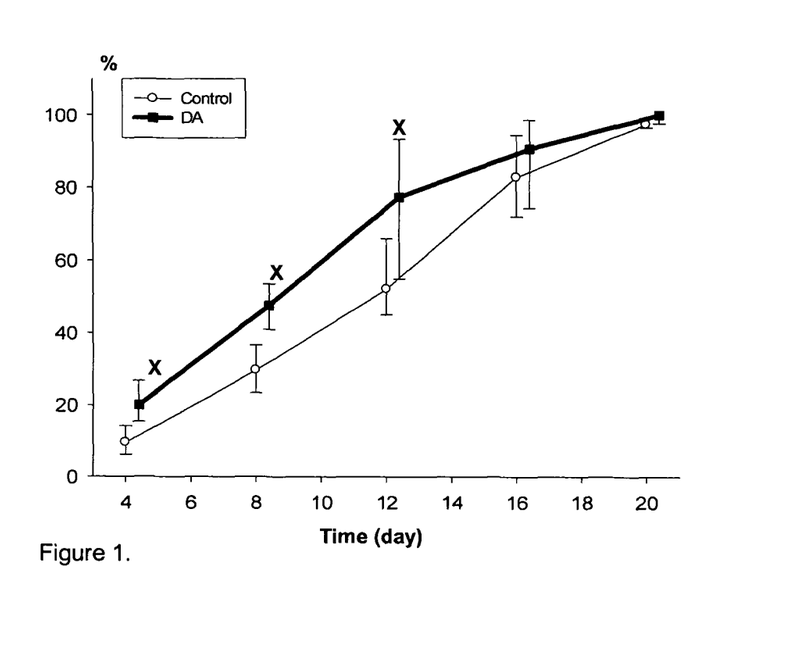
FIG. 1: Macroscopic wound closure in the control- and dantrolene-treated groups.

Macroscopic wound closure. This parameter reached nearly 100% in both groups by day 20. On days 4, 8, and 12, the rate of wound closure in dantrolene-treated groups was significantly higher than in control group. On day 16, no difference was found between the groups (FIG. 1).

Figure 2:
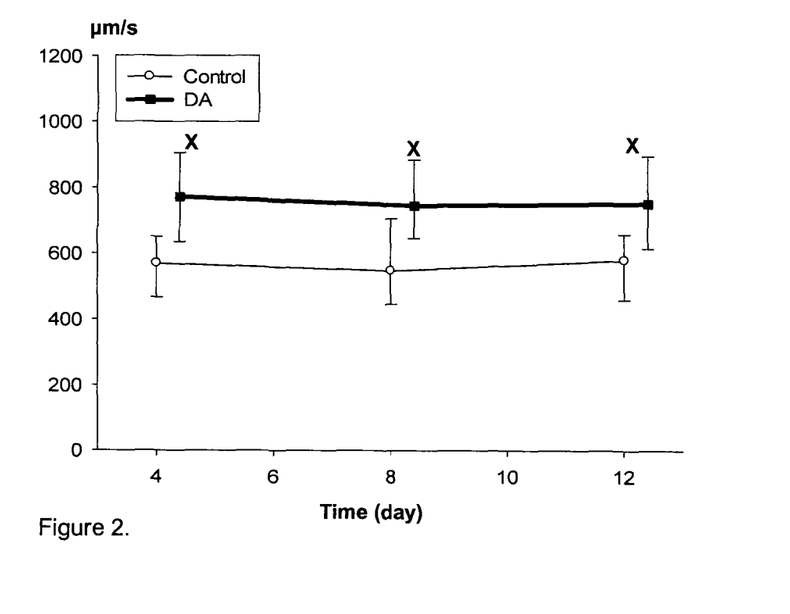
FIG. 2: Red blood cell velocity in the capillaries in the control- and dantrolene-treated groups.

RBCV in the capillaries. RBCV of dantrolene-treated animals was found be higher at all times of measurements (days 4, 8 and 12) than in control group (FIG. 2).

Figure 3:
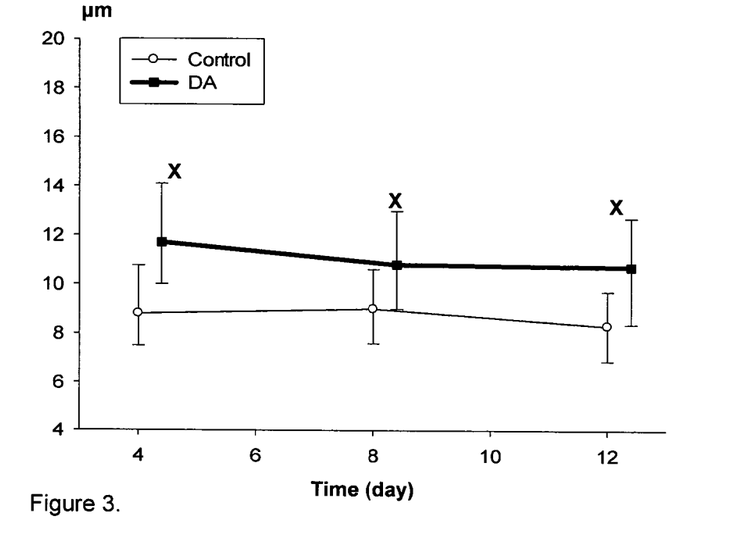
FIG. 3: Vessel diameters in the wound edges in the control- and dantrolene-treated groups.

Vessel diameters at the wound edges. Vessel diameters, determined at the wound edges of mice exposed to dantrolene, were considerably higher than those in the control group at corresponding times (FIG. 3).

Figure 4:
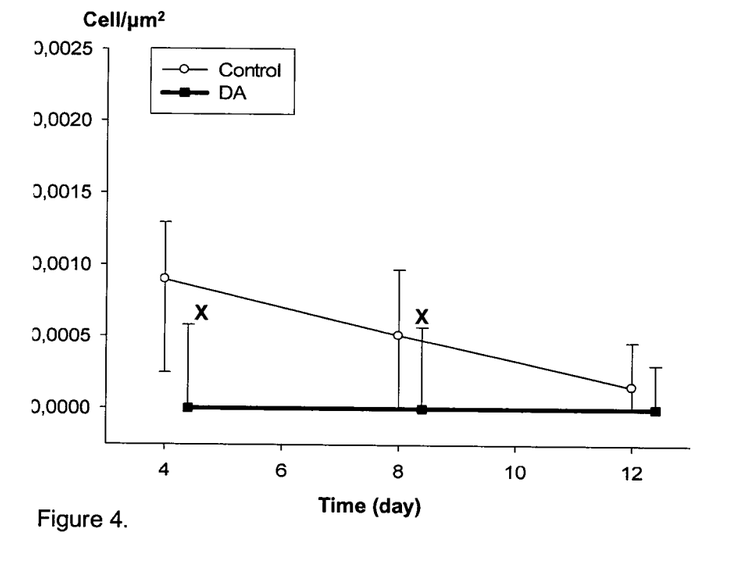
FIG. 4: Leukocyte adhesion in postcapillary venules in the control- and dantrolene-treated groups.

Sticking leukocytes in the postcapillary venules. Concerning leukocyte-endothelial interactions, said parameter was assessed as an indicator of inflammation. Our results revealed that application of dantrolene significantly decreased the number of sticking leukocytes on days 4 and 8. The difference on day 12 was not statistically significant (FIG. 4).

Figure 5:
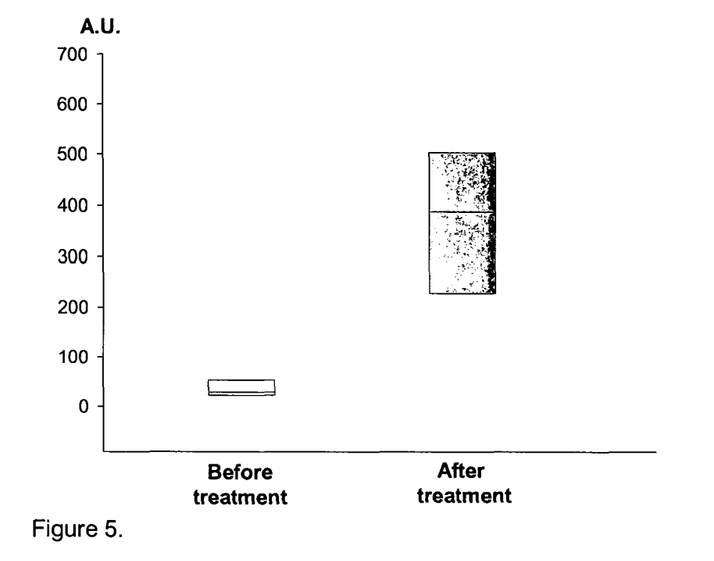
FIG. 5: Blood flow of the wound area determined with Laser Doppler before and after application of dantrolene.

Blood flow in the wound area. Laser Doppler flowmetry showed significant elevation in blood flow after dantrolene treatment (FIG. 5).

Figure 6:
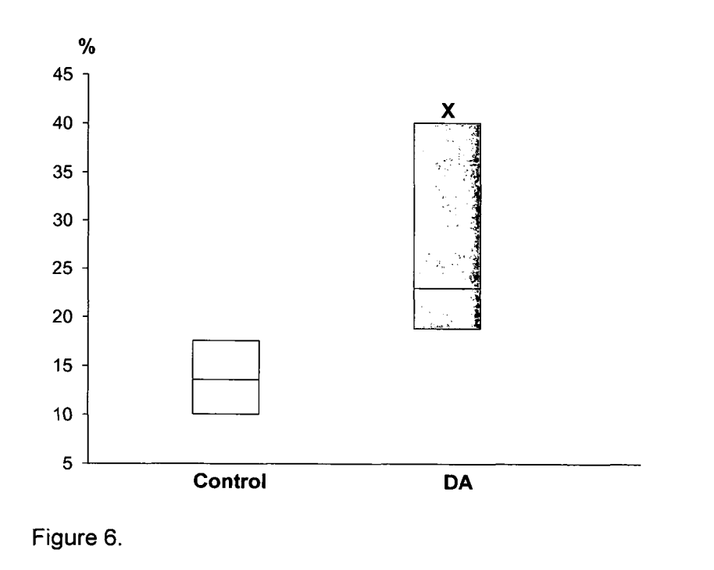
FIG. 6: Extension of epithelialization zone (relative to the initial diameter of the wound) in the control- and dantrolene-treated groups.

Extension of epithelialization zone. Epithelialization determined with routine histology (zone of epithelialization) was more extended in dantrolene-treated mice than in control ones on day 4 (FIG. 6).

Figure 7:
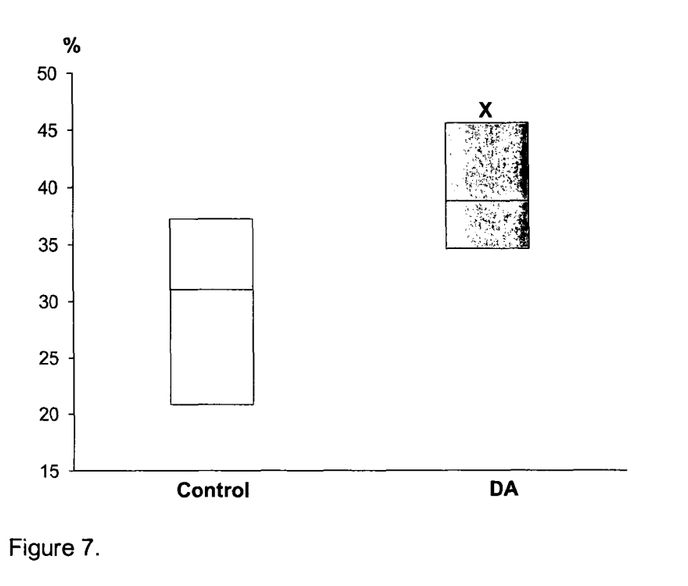
FIG. 7: Dermal regeneration (relative to the dermis of the intact skin) in the control- and dantrolene-treated groups.

Dermal regeneration. On day 4, said parameter was more expressed in animals receiving dantrolene than in control group (FIG. 7).

Example 2. Effect of Dantrolene on the Healing of Diabetic Wounds

The experiments will be performed on 12-15-week-old SKH-1 hairless mice of our own rearing (minimal weight: 30 g). Procedures and protocols were approved by the competent authorities (license number: V./145/2013.). Appropriate temperature (24+2° C.), 12 h dark-light cycles and free access to standard laboratory chow and water will be provided. Only healthy animals, free of any type of injury will be used, mice with any sign of disorders (except diabetes mellitus) will be discarded.

Interventions and Treatments:

According to recent data, diabetes mellitus can be induced with Streptozotocin (50 mg/kg intraperitoneally injected daily for 5 days) (Lee et al., 2014). 5 weeks after the induction of diabetes, the blood glucose level will be determined. Animals with blood glucose levels between 16.6 and 33.2 mmol/l will be accepted for the study (Langer et al., 2002). Prior to the interventions the animals will be anesthetized with an intraperitoneally administered mixture of ketamine (90 mg/kg) and xylazine (25 mg/kg). The ear will then be gently stretched. On the dorsal side of the ear, a circular area with a diameter of 2.5 mm will be marked. Using this mark, a full-thickness dermal layer will be excised down to the underlying cartilage by means of microsurgical scissors under a surgical microscope (Langer et al., 2002). The wound will be treated with a dantrolene-containing formulation (100 µM), while the control group will receive the vehicle, without the active agent. The observation period will take 15 days.

Examinations.

Macroscopic wound closure.

Photographs will be taken of the wounds immediately after surgery and on days 4, 7, 12, and 15. Circumstances of photographing will be standardized (same light sources and distances). The images will be evaluated with a software developed by our working group (DermAssess©). This software is an accessory function to the ImageJ software and enables the determination of color intensity (Eros et al., 2014) and the area measurement after calibration.

Intravital videomicroscopy (IVM): Microcirculation of the wound edges will be monitored by means of IVM on days 4, 7 and 12. After anesthesia, 80 µL of a solution of fluorescein-isothyocyanate (FITC) labeled dextrane (2%)

and also 80 μL of a solution of rhodamine-6G will be administered retrobulbar. These contrast materials allow us to visualize microcirculation and leukocyte-endothelial interactions at the appropriate wavelengths. Video records of the microcirculation will be evaluated off-line with Pictron IVM software. Red blood cell velocity (RBCV) will be determined in the capillaries, the diameter of each vessel in the evaluated fields-of-view will be measured (only diameters above 6 μm will be considered) and sticking leukocytes will be counted in the postcapillary venules (this parameter is relative to the area of the vessel wall and is given as cell/μm2).

Histology: On day 15 animals will be sacrificed, the wounds will then be excised, in order to be fixed in a solution of formaldehyde, embedded in paraffin and stained with hematoxylin and eosin. The Pannoramic Viewer software will be used for the evaluation. Zone of epithelialization will be defined as the extension of epithelial regeneration measured from the wound edges and given as percentage relative to the initial diameter of the wound.

REFERENCES

Daróczy J. és mtsai. A nem gyógyuló (krónikus) börsebek ellátásának előirányzott irányelve. A Bőrgyógyász Szakmai Kollégium jóváhagyásával készült irányelv 2011. átdolgozott formája. http://sebkezeles.hu/download/iranyelv.pdf Denda S, Kumamoto J, Takei K, Tsutsumi M, Aoki H, Denda M: Ryanodine receptors are expressed in epidermal keratinocytes and associated with keratinocyte differentiation and epidermal permeability barrier homeostasis. J Invest Dermatol 2012; 132: 69-75.

Kushnir A, Betzenhause M, Marks A R. Ryanodine Receptor Studies Using Genetically Engineered Mice. FEBS Lett 2010; 584(10):1956-1965.

Balschun D, Wolfer D P, Bertocchini F, Barone V, Conti A, Zuschratter W, Missiaen L, Lipp H P, Frey J U, Sorrentino V. Deletion of the ryanodine receptor type 3 (RyR3) impairs forms of synaptic plasticity and spatial learning. EMBO J. 1999; 18: 5264-73

Zucchi R, Ronca-Testoni S. The Sarcoplasmic Reticulum $Ca^{2+}$ Channel/Ryanodine Receptor: Modulation by Endogenous Effectors, Drugs and Disease States. Pharmacol Rev. 1997; 49: 1-52.

Arendshorst W J, Thai T L: Regulation of the renal microcirculation by ryanodine receptors and calcium-induced calcium release. Curr Opin Nephrol Hypertens 2009; 18:40-49.

Borisova L, Wray S, Eisner D A, Burdyga T: How structure, Ca signals, and cellular communications underlie function in precapillary arterioles. Circ Res 2009; 105:803-810.

Westcott E B, Jackson W F: Heterogeneous function of ryanodine receptors, but not $IP_3$ receptors, in hamster cremaster muscle feed arteries and arterioles. Am J Physiol Heart Circ Physiol 2011; 300:H1616-H1630.

Dabertrand F, Nelson M T, Brayden J E: Ryanodine receptors, calcium signaling, and regulation of vascular tone in the cerebral parenchymal microcirculation. Microcirculation 2012; 20:307-316.

Hess, Cathy Thomas "Clinical Guide to Skin and Wound Care" Seventh Edition, 2012.

Jaggar J H, Wellman GC, Heppner TJ, Porter VA, Perez GJ, Gollasch M, Kleppisch T, Rubart M, Stevenson A S, Lederer W J, Knot H J, Bonev A D, Nelson M T: $Ca^{2+}$ channels, ryanodine receptors and $Ca^{2+}$-activated $K^+$ channels: a functional unit for regulating arterial tone. Acta Physiol Scand 1998; 164:577-587.

Dabertrand F, Nelson M T, Brayden J E: Acidosis dilates brain parenchymal arterioles by conversion of calcium waves to sparks to activate BK channels. Circ Res 2012; 110:285-294.

Knot H J, Standen N B, Nelson M T: Ryanodine receptors regulate arterial diameter and wall [$Ca^2$] in cerebral arteries of rat by membrane potential and intravascular pressure. J Physiol 1998; 508(Pt I):211-221.

Shai Avi and Maibach Howard I. "Wound Healing and Ulcers of the Skin—Diagnosis and Therapy—The Practical Approach" 2005.

Sorg H, Krueger C, Vollmar B: Intravital insights in skin wound healing using the mouse dorsal skin fold chamber. J Anat 2007; 211:810-818.

www.ogyi.hu/kiseroirat/ah/ah_0000015827_20090323104723.doc

Harrison G C: Control of the malignant hyperpyrexic syndrome in MHS swine by dantrolene sodium. Br J Anaesth 1975; 47:62-65.

Erös G, Kurgyis Z, Németh I B, Csizmazia E, Berkó S, Szabó-Révész P, Kemény L, Csányi E: The irritant effects of pharmaceutically applied surfactants. J Surfact Deterg 2014; 17(1): 67-70.

Lee E, Kim D Y, Chung E, Lee E A, Park K S, Son Y: Transplantation of cyclic stretched fibroblasts accelerates the wound-healing process in streptozotocin-induced diabetic mice. Cell Transplant 2014; 23:285-301.

Langer S, Born F, Breidenbach A, Schneider A, Uhl E, Messmer K: Effect of C-peptide on wound healing and microcirculation in diabetic mice. Eur J Med Res 2002; 7:502-508.

The invention claimed is:

1. A method for treatment of a dermal wound associated with a chronic disease, said method comprising administering topically to a subject in need of such a treatment a pharmaceutical composition comprising as an active agent a ryanodine receptor antagonist compound of general formula (I)

wherein in formula (I)

Q is selected from halogen atoms, azido, thiocyano, nitro, amino, hydroxy, or $C_{1-4}$ alkyloxy;

$X_1$ is =CH— or =N—, $X_2$ is =CH— or =N—, $R_1$ is a hydrogen atom, $C_{1-4}$ alkyl, $C_{2-4}$ alkenyl, azido or amino; or $R_1$ is phenyl, benzyl or tolyl, and $R_2$ is a hydrogen atom, hydroxy, $C_{1-4}$ alkyloxy, $C_{1-4}$ alkyl, azido or amino.

2. The pharmaceutical composition for use according to claim 1, wherein in formula (I)

Q is selected from Br, Cl, F, nitro, unsubstituted amino, methylamino, dimethylamino, ethylmethylamino, hydroxy, methyloxy or ethyloxy, $X_1$ is =CH— or =N—, $X_2$ is =CH— or =N—, $R_1$ is a hydrogen atom, $C_{1-4}$ alkyl, $C_{2-4}$ alkenyl, the alkyl or alkenyl being unsubstituted or substituted, wherein the substituent is selected from the group consisting of I, Br, Cl and F, an unsubstituted amino, methylamino, ethylmethylamino or dimethylamino; or $R_1$ phenyl, benzyl or tolyl, being unsubstituted or substituted, wherein the substituent is selected from the group consisting of methyl, ethyl, propyl, isopropyl, I, Br, Cl, F, azido, hydroxy, unsubstituted amino, methylamino, ethylmethylamino and dimethylamino, and $R_2$ is a hydrogen atom, hydroxy, methyloxy or ethyloxy, $C_{1-4}$ alkyl, which is unsubstituted or substituted with a substituent selected from the group consisting of I, Br, Cl and F; unsubstituted amino, methylamino, ethylmethylamino or dimethylamino.

3. The method according to claim 1, wherein the compound of formula (I) is dantrolene or a pharmaceutically acceptable salt thereof.

4. The method according to claim 1, wherein the dermal wound is a wound that extends into a layer under the epidermis.

5. The method according to claim 4, wherein the dermal wound extends into all layers of the skin, including connective tissue, optionally connective tissue under the skin.

6. The method according to claim 1, wherein the dermal wound is associated with diabetes mellitus.

7. The method according to claim 1, wherein the pharmaceutical composition is in the form of an ointment, cream, gel, talcum, foam composition, patch, wound dressing, solution or suspension.

8. The method according to claim 1, wherein the pharmaceutical composition further comprises an additional active agent useful in wound healing.

9. The method according to claim 1, wherein the subject is a human or a vertebrate animal.

* * * * *